United States Patent [19]

Fujii et al.

[11] Patent Number: 4,867,974

[45] Date of Patent: Sep. 19, 1989

[54] AGENT FOR PREVENTING PLANT VIRUS DISEASES

[75] Inventors: Masahiro Fujii, Tokyo; Hiroshi Morita, Yokohama; Jun Hiraki, Yokohama; Masakazu Hatakeyama, Minamata, all of Japan

[73] Assignee: Chisso Corporation, Osaka, Japan

[21] Appl. No.: 67,419

[22] Filed: Jun. 22, 1987

[30] Foreign Application Priority Data

Jun. 24, 1986 [JP] Japan .................................. 61-146004

[51] Int. Cl.$^4$ ............................................. A61K 39/12
[52] U.S. Cl. ....................................... 424/89; 424/116; 514/2; 514/12; 530/300; 530/308; 530/806
[58] Field of Search ...................... 424/89, 116; 514/2, 514/12; 530/300, 308, 806

[56] References Cited

U.S. PATENT DOCUMENTS

| | | | |
|---|---|---|---|
| 3,215,684 | 11/1965 | Strojny et al. | 260/112 |
| 3,868,450 | 2/1975 | Harada et al. | 424/115 |
| 4,701,522 | 10/1987 | Susumu et al. | 530/370 |

FOREIGN PATENT DOCUMENTS 59-20359  5/1984  Japan .

OTHER PUBLICATIONS

Shima et al., "Poly-L-Lysine Produced by *Streptomyces*, Part III Chemical Studies", Agric. Biol. Chem., 45 (11), 2503–2508, 1981.

Shima et al., "Antimicrobial Action of ε-Poly-L-Lysine", J. of Antibiotics, XXXVII (11), 1449–1455, 1984.

Shima et al., "Inactivation of Bacteriophages by ε-Poly-L-Lysine Produced by *Streptomyces*", Agric. Bio. Chem., 46 (7), 1917–1919, 1982.

Hiramatsu et al., "Properties of Two Inhibitors of Plant Virus Infection from Fruiting Bodies of *Lentinus Edodes* and from Leaves of Yucca Recorvifolia Salisb." J. Biol. Chem., 51 (3), 897–904, 1987.

Tyihark et al., "Antagonistic Effect on Tobacco Mosaic Virus Infectivity Between Poly-L Lysine and Poly-L Arginine", 77:128050 BIOSIS.

*Primary Examiner*—John Kight
*Assistant Examiner*—S. Acquah
*Attorney, Agent, or Firm*—Browdy & Neimark

[57] ABSTRACT

Agent for preventing plant virus diseases such as tobacco mosaic viruses, potato viruses, cucumber mosaic viruses, etc. of this invention is obtained from a new agent containing polylysine as an active component. Polylysine can be used α-polylysine or β-polylysine.

5 Claims, No Drawings

AGENT FOR PREVENTING PLANT VIRUS DISEASES

BACKGROUND OF THE INVENTION

1. Fields of the Invention

This invention relates to an agent for preventing plant virus diseases. Particularly, this invention relates to an agent for preventing plant virus diseases characterized in that the agent contains polylysine as an active compound.

2. Related Art Statement

Once a plant is usually infected with a plant virus disease, the whole plant is infected and easily dead. The plant communicates the disease to other healthy plants one after the other by contact or entomophilous contagion, as the result, a great deal of damage is done to the plants before the plants are croped or removed. As the viruses of these plant pathogens, tobacco mosaic viruses (abbreviated as TMV) which infect eggplant family plants, potato viruses (abbreviated as PVX), cucumber mosaic viruses (abbreviated as CMV) which infect eggplant, cucumber or rape family plants can be exemplified.

As preventing ways of these virus diseases, for example, for entomophilous infection such as the cucumber mosaic diseases caused by CMV, extermination of intermediate insects, change of seeding time to avoid the insect generating time, cultivation of bred plants and so on have been tried. However, these methods are insufficient to obtain good control effect. For preventing the spread of virus diseases, infected plants have been pulled out. However, it is difficult to prevent the flying of poisonous insects from other fields, so that the prevention is not effective for such a trouble.

On the other hand, TMV diseases which do not infect by entomophily but by contact contagion infect crops at work by contacting the viruses with agricultural machines or by mixing the viruses into soil. For preventing the diseases, the agricultural machines, the soil, working clothes, fingers, etc. are subjected to disinfection at a great cost and expensive labor. However, such methods are insufficient to prevent the virus diseases.

Furthermore, TMV having weakened poison has been lately tried to use for preventing TMV-tomato. However, there is no guaranty that the TMV having weakened poison effectively acts on another kinds of crops. On the contrary, there is the possibility that a tomato which has contacted with the virus makes a contagion source and that viruses having strengthened poison are mixed into the viruses having weakened poison when many tomato seedlings are inoculated with the latter virus. For these reasons, no viruses having weakened poison have come into wide use.

As described above, physical elimination or agronomic control are only considered as a counterplan for preventing the plant virus diseases under existing circumstances. However, the control effect is little, and extensive damage caused by the plant virus diseases is done to crops. Accordingly, the prevention of the plant virus diseases is an important subject for agriculture.

For the purpose of inventing the prevention agent for plant virus diseases, many antiviral activates prepared from many natural products or synthetic compounds have been investigated. As the result, some materials having the antiviral activity have been found. Firstly, as a so-called multiplication control agent which controls virus multiplication in plant bodies, materials similar to nucleic acids such as 2-thiouracil, 8-azaguanine, 5-fluorouracil, etc. have been found. However, some of these materials wake some mutants and inhibit protein metabolism of hosts and give damages of medicine. These materials are generally expensive and have a little control effect in actual fields, so that these materials are not used in practice.

As an agent for blocking the contact contagion, sodium alginate is used. However, the application is limited to the TMV-OM and the control effect is insufficient. The agent is ineffective to entomophilous contagion virus such as CMV which is carried by plant lice such as aphid.

SUMMARY OF THE INVENTION

As a result of investigation of agents improving the above problems and having safety and good preventive effects, the present inventors have found that polylysine has the action for preventing the plant virus diseases and have completed the present invention.

The present invention provides an agent for preventing plant virus diseases, wherein the agent contains polylysine as an active component.

Polylysine which are used in the present invention is a polymer of lysine. Lysine is an essential amino acid having two amino groups in a molecule. Polylysine which is prepared from lysine comprises two types: $\alpha$-polylysine which is obtained by condensation of $\alpha$-amino groups and carboxyl groups and $\epsilon$-polylysine which is obtained by condensation of $\epsilon$-amino groups and carboxyl groups.

When polylysine is synthesized by a chemical method, $\alpha$-polylysin is usually obtained. The HBr salt of this $\alpha$-polylylsin is commercially available as a reagent from SIGMA Chemical Company, USA, and it can be used. On the other hand, $\epsilon$-polylysine is prepared by zymotechnics for instance. In this method, $\epsilon$-polylysine is obtained by incubation of a certain kind of microorganism belonging to Streptomyces under aerobic conditions (Japanese Patent Publication No. 59-20359).

Namely, No. 346-D strain (deposit No. 3834 of microorganisms of FRI) Streptomyces albulus subsp. lysinopolymerus, which belongs to Streptomyces genus and is a polylysine-producing actinomycetes, is incubated on culture medium. $\epsilon$-Polylysine can be obtained by separating and collecting from the resulting cultures. Naturally, the methods for producing polylysine which are used in the present invention are not limited at all.

The present invention is attainable its purpose in both cases using $\alpha$-polylysine and $\epsilon$-polylysine. However, $\epsilon$-polylysine is preferably used as an agent for preventing plant virus diseases. The reason is that although any polylysine can be used in accordance with the present invention, the effect of $\epsilon$-polylysine is slightly better than that of $\alpha$-polylysine for preventing the infection of virus diseases as shown in the following data. Accordingly, when the present invention is adopted, more desirable effect can be obtained by using $\epsilon$-polylysine.

TABLE 1

| | Effect of polylysine for preventing infection | |
|---|---|---|
| | Preventing rate of infection (TMV) | |
| Polylysine Concentration | $\alpha$-Polylysine hydrobromide | $\epsilon$-Polylysine hydrochloride |
| 200 ppm | 90% | 100% |
| 100 ppm | 65% | 91% |
| 50 ppm | 47% | 67% |

TABLE 1-continued

| | Effect of polylysine for preventing infection | |
|---|---|---|
| | Preventing rate of infection (TMV) | |
| Polylysine Concentration | α-Polylysine hydrobromide | ε-Polylysine hydrochloride |
| 25 ppm | 33% | 49% |

In this test, liquids having various concentrations of α-polylysine hydrobromide and ε-polylysine hydrochloride were prepared, and the same amount of TMV (2 μg/ml) was mixed into each liquid, then each mixture was inoculated into Samson NN tobacco by Carborundum method, and local lesions were counted. The concentrations of each polylysine are represented by the concentrations of free polylysine. As a control, an equivalent mixture of distilled water and virus was used.

The inhibition rates of infection were calculated by the following equation.

$$\text{Infection inhibition rate} = \frac{C - T}{C} \times 100\%$$

C: the number of local lesions of a control area
T: the number of local lesions of a test area As polylysine has a free amino acid in a constituent molecule of amino acid, polylysine can be used in the free form. Usually, it can be used as salts of inorganic or organic acids. In the case of α-polylysine, it can be obtained as HBr salts from restriction of materials which are used at synthetic reaction, but the other salts can be used if necessary. ε-Polylysine is frequently obtained in the form of hydrochloride, or it can be obtained as polylysine having a free form. In any form of a salt of an inorganic acid such as hydrochloride, sulfate, etc., a salt of an organic acid such as propionate, palmitate, etc., and so on, it can be used for the present invention.

For the preventive effects of polylysine to virus, the obstruction effect of virus multiplication can be exemplified in addition to the inhibition effect of infection as shown in Table 1. Namely, at first various concentrations of ε-polylysine hydrochloride were put into a petri dish (diameter 9 cm, liquid volume 20 ml), after TMV (2 μg/ml) and PVX (10 μg/ml) were inoculated into a leaf the day before, disks of 2 cm diameter were punched with a cork borer from the leaf infected by the virus, and the disks were floated on the petri dish. The virus was incubated under a natural light at room temperature for three days, then the disks were thoroughly washed with water and ground in a mortar containing ten times volume of 1% $K_2HPO_4$. The resultant liquid of TMV was inoculated into Samsun NN tobacco and the resultant liquid of PVX was inoculated into xanthine tobacco, and then the local lesions were tested. The result is shown in Table 2. As a control area, disks of the infection leaf were floated on distilled water.

TABLE 2

| Abstruction effect of virus multiplication | | |
|---|---|---|
| ε-Polylysine concentration[1] | TMV | PVX |
| 200 ppm | 46% | 61% |
| 100 ppm | 44% | 63% |
| 50 ppm | 6% | 39% |
| 25 ppm | 0% | 15% |

[1]These concentration are set on the basis of free ε-polylysine concentration

Thus, when the concentration of ε-polylylsine is above 100 ppm the obstruction effect shows around 50%.

Methods for preventing plant virus diseases by using polylysine of this invention are as follows.

(1) 10 to 500 ppm of aqueous solutions of polylysine are sprayed or applied on plants to be prevented.
(2) While working by polling the top, nipping the bud, binding props, etc., workers disinfect agricultural tools such as shears and their fingers by 100–500 ppm of aqueous polylysine solutions whenever they treat a few crops.
(3) Before sowing is carried out, seeds are dipped into 100–500 ppm of polylysine solution for a definite time.

Especially, for the contagion virus, before the agricultural work such as polling the top, nipping the bud, binding props, inducing etc., it is effective to spray with the polylysine aqueous solution on every desired plant.

As the virus diseases which can be prevented by using the polylysine of the present invention as a preventing agent of plant viruses, in addition to the above TMV, PVX, etc., CMV (cucumber mosaic virus), WMV (pumpkin mosaic virus), TuMV (turnip mosaic virus), CaMV (cauliflower mosaic virus), etc. can be exemplified.

When the plant virus diseases caused by these viruses are controlled, in order to heighten the preventive effect, (1) simultaneous use of a spreader for an agricultural medicine and the preventing agent of this invention, or
(2) simultaneous use of a preventing agent of plant lice such as aphid and the preventing agent of the present invention can be conducted. The simultaneous use or preparation can exceed the simple use of the polylysine of this invention in the preventive effect.

When the polylysine of the present invention is used as a preventing agent of plant virus diseases, its advantage is the enhanced safety and the heightened preventive effect. When the hydrochloride of ε-polylysine which is used in the present invention is orally dosed to a mouse, the acute toxicity is above 5 g/kg in $LD_{50}$. Furthermore, the polylysine of this invention is normal in a mutagen test with micro-organisms, a primary test of skin stimulus with rabbits, and a primary test of eye mucosa stimulus.

As described above, the preventing agent of plant virus diseases of the present invention in which polylysine is used shows more excellent preventive effect than that of conventional preventing agents, so that it can be prevented that useful plants are damaged by virus. The efficiency effect can be also heightened while at work in agriculture. Thus, the agent of the present invention can produce practical results.

DESCRIPTION OF THE PREFERRED EMBODIMENTS

EXAMPLE 1

α-Polylysine-hydrobromide aqueous solution which was adjusted to concentration of 200 ppm based on α-polylysine was sprayed on every leaf of a potted tobacco seedling (Samsun NN breed) at the period of 12 leaves. Thirty minutes after spraying, previously prepared TMV (1 μg/ml) was inoculated in sap of leaves with carborundum in the usual way.

Four days after the inocuration, local lesions were examined and the infection inhibition rates for TMV were calculated in accordance with the method described in Table 1.

As a control agent, 5000 ppm of sodium alginate in aqueous solution was used.

Five roots per group were used in a test, and the test was repeated twice. The test results are shown in Table 3.

TABLE 3

| Used agent | Concentration (ppm) | Infection inhibition rate (%) | Medical damage |
|---|---|---|---|
| α-polylysine hydrobromide | 200[1] | 86 | nothing |
| Control agent (Sodium alginate) | 5000 | 55 | nothing |
| non-treatment | — | 0 | nothing |

[1]Concentration based on α-polylysine

EXAMPLE 2

Two hundreds mg of ε-polylysine and 100 mg of sodium lauryl sulfate were homogeneously made up to 1 liter with water (aqueous solution of 200 ppm of ε-polylysine).

The aqueous solution of 200 ppm of ε-polylysine which was prepared as described above was sprayed on every leaf of a potted tobacco (xanth-NC breed) seedling at the period of 10 leaves. One hour after spraying, previously prepared PVX (5 μg/ml) was inoculated in sap of leaves with carborundum in the usual way. Four days after the inoculation, local lesions were examined and the infection inhibition rates for PVX were calculated in accordance with the same manner as Example 1.

Five roots per group were used in a test, and the test was repeated twice. The test results are shown in Table 4.

TABLE 4

| Used agent | Concentration (ppm) | Infection inhibition rate (%) | Medical damage |
|---|---|---|---|
| ε-Polylysine aqueous soln. | 200[1] | 99 | nothing |
| Non-treatment | — | | nothing |

[1]Concentration based on ε-polylysine

EXAMPLE 3

Two hundreds mg of ε-polylysine and 200 mg of xanthan gum were homogeneously made up to 1 liter with water (aqueous solution of 200 ppm of ε-polylysine). The above-mentioned ε-polylysine aqueous solution of 15 ml per pot was sprayed on every seed leaf of a potted cucumber seedling after five days since it germinated. One hour after spraying, CMV was inoculated in sap of leaves with carborundum in the usual way. Fourteen days after the inoculation, the number of roots having mosaic-lesions which were appeared on the cucumber seedling were examined and the infection inhibition rates (%) were calculated in accordance with the following formula.

Ten roots per area were used in a test at a hothouse and the test was repeated twice.

$$\text{Infection inhibition rate} = \frac{C - T}{C} \times 100\%$$

C: the number of mosaic-lesions of a non-treated area
T: the number of mosaic-lesions of a treated area The results are shown in Table 5.

TABLE 5

| Used agent | Concentration (ppm) | Infection inhibition rate (%) | Medical damage |
|---|---|---|---|
| ε-Polylysine aqueous soln. | 200[1] | 100 | nothing |
| Non-treatment | — | 0 | nothing |

[1]Concentration based on ε-polylysine

EXAMPLE 4

Pimentos were cultivated and wintered in the house where pimentos had caught the tobacco mosaic disease in last planting. The pimentos had been set out at the beginning of October in the house. ε-Polylysine hydrochloride aqueous solution (250 ppm based on ε-polylysine) was repeatedly sprinkled on the pimentos in the proportion of 20 liter per are every seven days from one week after that the pimentos had been set out. After sprinkling the solution, inducement work was conducted and the pimentos were harvested by a plucking method. The solution was sprinkled 20 times up to March. The generating rate of disease roots was finally 36%. On the contrary, the generating rate of disease roots was 100% at a non-sprinkled area. The harvest rate of the area sprinkled ε-polylysine hydrochloride increased at the rate of 32% in comparison with the non-sprinkled area.

The results are shown in Table 6.

TABLE 6

| Test area | Generating rate of disease roots (%) | Harvest[2] (kg) | Medical damage |
|---|---|---|---|
| ε-Polylysine hydrochloride -sprinkled area[1] | 36 | 5.55 | nothing |
| Non-sprinkled area | 100 | 4.19 | nothing |

[1]Concentration is 250 ppm based on ε-polylysine in aqueous solution.
[2]Harvest of one area per seven roots.

EXAMPLE 5

The test was conducted under the same conditions as in Example 1 except that ε-polylysine acetate was used in the place of α-polylysine hydrobromide.

Four days after the inocuration, local lesions were examined and the infection inhibition rates for TMV were calculated in accordance with the method described in Table 1. As a control agent, 5000 ppm of sodium alginate in aqueous solution was used.

Five roots per group were used in a test, and the test was repeated twice.

The test results are shown in Table 7.

TABLE 7

| Used agent | Concentration (ppm) | Infection inhibition rate (%) | Medical damage |
|---|---|---|---|
| ε-Polylysine acetate | 200[1] | 95 | nothing |
| Control agent (Sodium alginate) | 5000 | 55 | nothing |
| Non-treatment | — | 0 | nothing |

[1]Concentration based on ε-polylysine

What is claimed is:

1. A method for preventing viral diseases in plants, comprising the step of applying epsilon polylysine or a salt thereof to a plant.

2. The method of claim 1, wherein said epsilon polylysine is applied as solution.

3. A method as claimed in claim 2, wherein the concentration of said epsilon polylysine in said solution is 10–10,000 ppm.

4. A method as claimed in claim 1, wherein said epsilon polylysine is a salt of an organic acid or an inorganic acid.

5. The method of claim 2, wherein said applying is performed by spraying or inoculation.

* * * * *